United States Patent
Monot et al.

(12)

(10) Patent No.: US 6,337,204 B1
(45) Date of Patent: Jan. 8, 2002

(54) BIOLOGICAL CULTURE CONTAINING *RHODOCOCCUS ERYTHROPOLIS ERYTHROPOLIS* AND/OR *RHODOCOCCUS RHODNII* AND PROCESS FOR DESULFURIZATION OF PETROLEUM FRACTION

(75) Inventors: Frédéric Monot, Nanterre; Samir Abbad-Andaloussi, Paris; Michel Warzywoda, Rueil Malmaison, all of (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/597,469

(22) Filed: Jun. 19, 2000

(30) Foreign Application Priority Data

Jun. 17, 1999 (FR) ............................................ 99-07807

(51) Int. Cl.$^7$ .............................................. C10G 32/00
(52) U.S. Cl. ....................................... 435/282; 435/262
(58) Field of Search .................................. 435/262, 282

(56) References Cited

U.S. PATENT DOCUMENTS 6,071,738 A * 6/2000 Johnson et al. ............. 435/282

FOREIGN PATENT DOCUMENTS

| WO | WO 98 04678 | 2/1998 |
| WO | WO 98 45446 | 10/1998 |

OTHER PUBLICATIONS

"Enzymes Desulfizing Fuel In Pilot Tests", Oil and Gas Journal, U.S. Pennwell Publishing Co. Tulsa, vol. 93, No. 20, May 15, 1995 (May 15, 1995), pp. 39–40, XP000513425.

* cited by examiner

Primary Examiner—Herbert J. Lilling
(74) Attorney, Agent, or Firm—Millen, White, Zelano & Branigan, P.C.

(57) ABSTRACT

This invention relates to a biological culture comprising at least one bacterial strain that is selected from the group that is formed by

*Rhodococcus erythropolis* CNCM I-2204
*Rhodococcus erythropolis* CNCM I-2205
*Rhodococcus erythropolis* CNCM I-2207
*Rhodococcus erythropolis* CNCM I-2208
*Rhodococcus rhodnii* CNCM I-2206 able to selectively attack the C—S bonds of organic molecules present in hydrocarbons without substantially altering their carbon structure, and having improved stability.

The invention also relates to a process for desulfurization of a hydrocarbon feedstock containing sulfur-containing organic molecules.

16 Claims, No Drawings

BIOLOGICAL CULTURE CONTAINING *RHODOCOCCUS ERYTHROPOLIS ERYTHROPOLIS* AND/OR *RHODOCOCCUS RHODNII* AND PROCESS FOR DESULFURIZATION OF PETROLEUM FRACTION

This invention relates to five pure strains of *Rhodococcus erythropolis* CNCM I-2204, *Rhodococcus erythropolis* CNCM I-2205, *Rhodococcus erythropolis* CNCM I-2207, *Rhodococcus erythropolis* CNCM I-2208, and *Rhodococcus rhodnii* CNCM I-2206 that can selectively eliminate organic sulfur from sulfur-containing organic molecules present in certain fossil fuels, and their use in processes for desulfurizing these fuels, in particular petroleum and some of its fractions and their derivatives.

In addition to carbon, fossil fuels such as coal and petroleum contain other elements, such as, for example, sulfur and nitrogen. Thus, crude oil contains sulfur, mainly in organic form, in more or less high concentrations, in general between 0.025% and 5%. This sulfur still remains in a more or less high ratio in the petroleum fractions obtained by distillation (for example up to 10% in certain heavy fractions), and subsequently also in the various petroleum products. In crude oil, sulfur is present mainly in the form of organic sulfur (sulfides, thiols, thiophene, benzothiophene, dibenzothiophene and their substituted derivatives). In several crude oils such as Texas crude, about 70% of the organic sulfur is present in the form of dibenzothiophene (DBT) or alkylated derivatives of DBT.

Combustion of the sulfur present in the fuels causes formation of sulfur dioxides that give rise to acid rain and that are considered to be among the worst air pollutants. In order to limit these noxious emissions, legislation has set standards for sulfur content in petroleum fuels. Moreover, these standards are becoming increasingly strict. For example, the nations of the European Union decided to set the upper limit of gasoil sulfur content at 350 ppm in the year 2000 and it will probably be around 50 ppm in the year 2005. The current specifications for gasoil have been 500 ppm since October 1996, and the preceding specification was 0.2%.

Such specifications dictate accelerated desulfurization of petroleum products by high-performing and economical processes.

Conventional desulfurization processes used in the refining industry implement physico-chemical hydrodesulfurization techniques which allow the reduction of the C—S bonds in hydrogen sulfide ($H_2S$). This reaction is catalyzed by metallic catalysts and takes place in the presence of hydrogen at a high temperature. The deep desulfurization processes required by the new standards call for working at higher temperatures and at increasingly higher partial hydrogen pressures, and lengthening the dwell time in the reactors. All these factors considerably increase the cost of the desulfurization process. In addition, to attain very low sulfur contents, it is becoming necessary to remove the most refractory sulfur compounds in hydrodesulfurization. To use the example of gasoil, the most refractory compounds are often represented by DBT and its derivatives. It is therefore necessary to increase the hydrogen pressure, the temperature and the dwell time to attain low sulfur contents, thereby considerably increasing operating costs. Moreover, hydrodesulfurization operating conditions can sometimes be so strict that a possible degradation of hydrocarbons other than said sulfur-containing compounds results. Finally, in certain cases, the high concentration of heavy metals in the petroleum may limit the use of hydrodesulfurization catalysts which are sensitive to the presence of the latter. Since the heavy metal concentration and sulfur concentration often increase in a parallel manner during refining, this problem may also limit the implementation of hydrodesulfurization processes.

This is why the development of processes for desulfurization of petroleum or at the very least of some petroleum compounds other than chemical hydrodesulfurization has been studied for several years. This is particularly the case of biological processes that are still called biodesulfurization (BDS) processes.

Several methods of microbiological desulfurization have been described in the literature. Thus, certain sulfate-reducing anaerobic microorganisms are able to degrade DBT with production of $H_2S$. These are slow processes that require reducing elements that may be supplied electrochemically as described in U.S. Pat. No. 4,954,229 or in the form of molecular hydrogen.

There are microorganisms that can aerobically oxidize DBT. In the majority of cases, such systems degrade DBT by using the so-called Kodama metabolic method (Kodama et al., Agr. Biol. Chem., 34, 1320, (1970)). In this case, there is no actual desulfurization, since oxidation is accomplished on one of the aromatic cores of DBT without the final product losing its sulfur atom. Likewise, there are microorganisms that can aerobically mineralize DBT (Kropp and Fedorak, Canad. J. Microbiol., 44, 605 (1998)). The use of these microorganisms for desulfurization purposes is not considered, because a significant loss of calorific power of the fuel thus treated would result therefrom.

The discovery of the strain Rhodococcus sp. IGTS8 (ATCC No. 53968) described in U.S. Pat. No. 5104801 allowed biodesulfurization to be considered as a conceivable proces that can be economically advantageous. This strain can aerobically remove sulfur from dibenzothiophene by specific oxidation of sulfur using the so-called 4S metabolic method (sulfoxide, sulfone, sulfinate, sulfite or sulfate). The final product resulting from desulfurization of DBT is 2-hydroxybiphenyl, and the sulfur is released in the form of sulfite (Oldfield et al., Microbiology, 143, 2961 (1997)). This new metabolic method was the subject of numerous studies. The DBT desulfurization phenotype is conferred by a dsz operon located on a plasmid. This operon codes for three enzymes, Dsz A, B and C, which are responsible for the oxidation reactions of DBT in hydroxybiphenyl (Li et al., J. Bacteriol., 178, 6409 (1996)). This operon was cloned and sequenced, and the metabolic method was described (Piddington et al., Appl. Environm. Microbiol., 61, 468 (1995)). A fourth enzyme, DszD, which acts to transport electrons, is also involved in this metabolism (Xi et al., Biochem. Biophys. Res. Commun., 230, 73 (1997)). These different enzymes have been purified and characterized (Gray et al., Nature Biotechnol., 14, 1705 (1996)). Genetic analysis revealed the existence of a promoter and activity regulation mechanisms. Thus, the expression of genes in the 4S method is suppressed by sulfur that is easily available such as sulfate, cysteine or methionine. Many patents have been filed on the use of the IGTS8 strain.

Since the isolation of the IGTS8 strain was described, several other groups of researchers reported the isolation of other strains able to use the 4S method by enrichment on a minimum mineral medium containing only DBT as a sulfur source. It is thus possible to cite Rhodococcus sp. SY1 (Omori et al., Biosci. Biotechnol. Bioeng., 59, 1195 (1995)) first described as being a Corynebacterium (Omori et al., Appl. Environm. Microbiol., 58, 911 (1992)), *Rhodococcus*

*erythropolis* D-1 (Izumi et al., Appl. Environm. Microbiol., 60, 223 (1994)), *Rhodococcus erythropolis* H-2 (Ohshiro et al., FEMS Microbiol. Lett., 142, 65 (1996)), Rhodococcus UM3 and UM9 (Purdy et al., Curr. Microbiol., 27, 219 (1993)), *Rhodococcus erythropolis* (Wang and Krawiec, Arch. Microbiol., 161, 266 (1994)), Mycobacterium sp. strain G3 (Nekodzuka et al., Biocatal. Biotrans., 15, 17 (1997)), Paenibacillus sp. strain A11-1 and A11-2 (Konishi et al., Appl. Environm. Microbiol., 63, 3164 (1997)) which have the particular characteristic of being thermophilic, *Arthrobacter paraffineus* ECRD-1 (Lee et al., Appl. Environm. Microbiol., 61, 4362 (1995)) which was reclassified as actually being a Rhodococcus (Denis-Larose et al., Appl. Environm. Microbiol., 63, 2915 (1997)) and which was isolated on 4,6-diethyl dibenzothiophene, Arthrobacter sp. (E.P. 795603) which has the particular characteristic of acting on petroleum products without the addition of surfactants, Gordona CYSKI (Rhee et al., Appl. Environm. Microbiol., 64, 2327 1998), Sphingomonas sp. strain AD109 (PCT 98/45446).

Rhodococcus sp. IGTS8 has a number of properties which have made it particularly attractive for development in a biodesulfurization process (U.S. Pat. Nos. 5,104,801, 5,132,219, 5,198,341, 5,232,854, 5,344,778, 5,356,801, 5,356,813, 5,358,869, 5,358,870, 5,387,523, 5,472,875, 5,496,729, 5,510,265, 5,516,677, 5,529,930, 5,578,478, 5,733,773, 5,772,901, 5,811,285, . . . ). Implementation of such a process consists of several stages:

1) Cultivating the selected strain in a fermenter in the presence of carbon sources and other nutrients in such a way as to obtain the largest possible number of microorganism cells having the highest possible level of activity;

2) Harvesting these cells (separation of the bacterial biomass from the culture medium);

3) Using these cells in the form of "resting cells," i.e., non-proliferating cells, in a biodesulfurization process during which enzymatic reactions take place that allow the organic sulfur of the feedstock to be treated to be transformed into sulfate or sulfite. This stage takes place in the presence of an aqueous phase;

4) Separating the different phases (oil, sulfate-loaded aqueous phase, biocatalyst solid phase);

5) Recycling all or part of the biocatalyst by adding new biocatalyst to it in such a way as to obtain sufficient activity;

6) Removing water from the desulfurized oil phase;

7) Removing sulfate from the aqueous phase.

To be used in an industrial process, however, any biodesulfurization biocatalyst must have sufficient stability.

Here, stability is defined as the stability of the biocatalyst during the biodesulfurization operation itself and not the stability of the strain (i.e., its preservation). From the economic standpoint, it is important to work in stage 3 with the most stable biocatalyst possible, with the price of the biocatalyst comprising a large part of the overall cost of the process. The stability, like the activity itself, is one of the key parameters in the viability of a biodesulfurization process. The cost of the process is directly proportional to it. Thus, a continuous biodesulfurization operation would only be seriously considered if a sufficiently stable biocatalyst were used. In addition, this also makes it possible to avoid the need to repeatedly add biocatalyst. In the case of a batch operation, the potential length of the operation and therefore the amount of substrate which will be treated will depend on the operating stability of the biocatalyst. It is known, however, that the strains that have been described for use in a biodesulfurization process have limited stability. Thus, strain IGTSB is described as having a half-life of 6 to 10 hours at 30° C. ("Commercial Development Progress Report & Market Update on Biocatalytic Desulfurization (BDS)", by J. A. Nagel presented at "the Catalytic Advances Program Meeting, Feb. 25–26, 1996). Half-life is defined as the time at the end of which the biocatalytic system has lost half its initial activity. Strains having desulfurization activity that are much more stable over time would allow substantial cost advantages.

Another patent such as WO 98 45446 describes the use of a strain of Sphingomonas to desulfurize fuels containing organosulfur-containing molecules. Another patent, WO 98 04678, describes the use of two strains of Rhodococcus, 213E and 213F, selected for their action on benzothiophene, whereby strain 213 F can desulfurize dibenzothiophene. Neither of these patents, however, describes or suggests a solution to the problem of the feasibility of using a biodesulfurization process on an industrial scale, i.e., the search for stable strains.

This invention is based on the discovery, isolation and use of new bacterial strains that can selectively attack the C—S bonds of organic sulfur-containing molecules present in carbon products without altering the carbon structure of these molecules, and that would be stable enough to allow the aforementioned disadvantages to be avoided when using the strains in a biodesulfurization process.

Samples of these strains were submitted on May 20, 1999 to the National Collection of Microorganism Cultures of the Pasteur Institute (CNCM) under the numbers I-2204, I-2205, I-2206, I-2207, I-2208.

The strains described in this patent were isolated from soil samples taken from various coal storage sites. The isolation was performed by successive enrichment phases in a liquid medium and purification on a culture medium containing various sources of carbon (glycerol, glucose, succinate, ethanol) and dibenzothiophene as the only sulfur source. Special attention was focused on the composition of this medium to ensure that it would not contain any trace of sulfur other than the DBT. It is a specific minimum synthetic medium that does not contain any source of organic nitrogen and whose purity of components was selected such that the concentration of the sulfates in the medium is the lowest possible. From the various samples, fifteen or so pure strains that can use DBT as a single sulfur source were isolated.

We then eliminated the strains for which the product of degradation of DBT in the liquid medium was not hydroxybiphenyl (HBP). Thus, we kept only the strains that can degrade the DBT using the 4S method. To confirm this hypothesis and to evaluate the desulfurization activity (rate of disappearance of DBT by non-proliferating cells) of these strains, we cultivated them on the usual culture medium (minimum medium in the presence of DBT) in flasks, then we recovered the cells by centrifuging, and after washing with phosphate buffer and centrifuging, we used these cells in bioconversion as "resting cells" on DBT. The reaction products were then analyzed by HPLC after addition of acetonitrile in the conversion medium. Concentrations of residual DBT and the HBP formed could thus be determined. Only the strains leading to an activity level greater than 1 mg of DBT degraded per gram of cells (dry weight) per hour were retained.

Thus having ten or so strains having DBT desulfurization activity using the 4S method, we selected the most stable strains. The stability of the activity of the strains was determined by incubation of "resting cells" harvested after culturing the different strains under similar conditions. The initial activity of the cells was estimated using the conventional method. Then, the cells were incubated in the DBT-free conversion medium at 30° C. while being stirred. The activity of cells after different incubation times at 30° C. while being stirred was determined in the usual way after simple addition of DBT in the incubation medium to initiate the desulfurization reaction. This activity was then compared to the activity the cells had initially exhibited for the purpose of evaluating stability. This criterion is essential in terms of the process because it reflects the operating stability of the desulfurization system under pH and temperature conditions similar to operating conditions. These two parameters, however, are known to have a dramatic effect on the stability of enzymatic systems.

Based on this criterion, only five strains were selected. The selection criterion is based on residual DBT desulfurization activity that is at least equal to 10% of the initial activity after 96 hours of incubation in an aqueous medium at 30° C. and at a pH of 7. Advantageously, the strains selected can have a residual DBT desulfurization activity after 96 hours of incubation in an aqueous medium at 30° C. and at a pH of 7 of at least 30%, preferably at least 50%, most often at least 70%. Moreover, these strains have good stability in a two-phase water/oil medium, a medium that represents the desulfurization conditions of petroleum feedstocks.

These five pure strains have been characterized. They were subjected to a morphological examination by optical microscopy, using Gram staining as well as various biochemical tests.

| Test type | I-2204 | I-2205 | I-2206 | I-2207 | I-2208 |
|---|---|---|---|---|---|
| Gram | + | + | + | + | + |
| Morphology | coryne-form bacillus | coryne-form bacillus | coryne-form bacillus | coryne-form bacillus | coryne-form bacillus |
| Mobility | no | no | no | no | no |
| Sporulated shape | no | no | no | no | no |
| Capsule | no | no | no | no | no |
| Branching | no | no | no | no | no |
| Growth on ordinary nutrient media (24 hours at 30° C. | low | yes | yes | yes | yes |
| Pigmentation | slight pink pigmentation | no | pink | no | no |
| Respiratory metabolism | uninterpretable | strictly aerobic | strictly aerobic | strictly aerobic | uninterpretable |
| Catalase | + | + | + | + | + |
| Reductase nitrate | + | − | − | − | − |
| Urea | + | + | + | + | + |
| Esculine | + | + (Delayed) | + | + | + (to a small degree) |
| Amylase | − | − | − | − | − |
| Dnase | − | − | − | − | − |
| Proteolysis | − | + (to a small degree) | − | − | − |
| Tween-80-esterase | − | − | + | + | + |

The strains were then characterized by using them on API coryne galleries intended for identification of coryneform bacteria such as those described in this invention:

| Type of test | I-2204 | I-2205 | I-2206 | I-2207 | I-2208 |
|---|---|---|---|---|---|
| Reduction of nitrates | + | + | − | − | − |
| Pyrazinamidase | + | + | + | + | − |
| Arylamidase pyrrolidonyl | − | − | − | − | − |
| Alkaline phosphatase | + | + | + | + | + |
| β-glucuronidase | − | − | − | − | − |
| β-galactosidase | − | − | − | − | − |
| α-glucosidase | + | + | + | + | + |
| N-acetyl-β-glucosaminidase | − | − | − | − | − |
| Esculine (β-glucosidase) | + | − | + | + | + |
| Urease | + | + | + | + | + |
| Gelatin (hydrolysis) | − | − | − | − | − |
| Fermentation of: | | | | | |
| glucose | − | − | − | + | − |
| ribose | − | − | − | − | − |
| xylose | − | − | − | − | − |
| mannitol | − | − | − | − | − |
| maltose | − | − | − | − | − |
| lactose | − | − | − | − | − |
| saccharose | − | − | − | − | − |
| glycogen | − | − | − | − | − |
| Catalase | + | + | + | + | + |

Based only on these characteristics, it was difficult to identify these strains precisely. That is why additional chemical-taxonomic analyses had to be performed. They consisted of an analysis of the composition of the bacterial walls and an overall analysis of the protein content of the cells.

Determination of the type of peptidoglycane did not reveal any major difference between the five strains, whereby the connecting diamino acid is meso-diaminopimelic acid (determination by thin-layer chromatography or TLC). The constituent sugars of the polymers of the wall are arabinose, galactose and glucose (TLC analysis). The five layers contain the same sugars and have no significant differences. They contain all five of the mycolates and the I-2206 strain differs in that it has one mycolic acid with a higher mobility (TLC analysis). The polar lipids are analyzed by thin layer chromatography which specifically shows phosphorylated lipids, aminated lipids and glycosylated lipids, as well as total lipids. The presence of phosphatidyl glycerol, phosphatidyl ethanolamine, and phosphatidyl inositol is also demonstrated in the five strains. Finally, these five strains have very similar peripheral characteristics. comparison with the databases reveals that they belong to the Rhodococcus/Gordona group. To refine the identification, an evaluation of the electrophoretic profile of the total proteins of each of the five strains was carried out ("sodium dodecyl sulfate polyacrylamide gel electroporesis" or SDS-PAGE). The isolates were classified by digital analysis of the total protein profiles and comparison with the profile base. The four isolates I-2204, I-2205, I-2207 and I-2208 are included in the taxon *Rhodococcus erythropolis*, while I-2206 is grouped with the *Rhodococcus rhodnii*/Gordona cluster. As for I-2206, since it is more similar to database strains belonging to the *Rhodococcus rhodnii* species than to the Gordona strains referenced in the database, it appeared more logical to us to call it *Rhodococcus rhodnii*.

More specifically, the invention relates to a process for desulfurization of a hydrocarbon feedstock containing organic sulfur-containing molecules using a bacterial culture in the presence of water and in an oxidizing atmosphere, at a temperature of between 20 and 40° C., and at a pH of between 5 and 9, characterized in that it comprises the following stages:

a) The feedstock and the aqueous phase are brought into contact with the biological culture that comprises at least one bacterial strain formed by
*Rhodococcus erythropolis* CNCM I-2204
*Rhodococcus erythropolis* CNCM I-2205
*Rhodococcus erythropolis* CNCM I-2207
*Rhodococcus erythropolis* CNCM I-2208
*Rhodococcus rhodnii* CNCM I-2206
or with its enzymatic derivatives, thereby obtaining a reaction medium;

b) a desulfurized oily phase that is recovered and an aqueous phase containing the biological culture are separated from the reaction medium, and c) the aqueous phase in stage (a) is at least partially recycled.

The reaction medium may comprise an emulsified phase that comprises said biological culture, the aqueous phase and the oily phase, and said emulsified phase is separated from the reaction medium and recycled at least in part in stage a).

According to another characteristic, the aqueous phase may contain sulfates that can be eliminated using conventional techniques that are described, for example, above.

The desulfurization process using these strains may consist in bringing the strain or the enzymatic complex (crude extract) that has been isolated from any one of these strains into contact with the substrate that must be desulfurized in the presence of water. The amount of water present can be very low or high. It may be an emulsion or a non-emulsified two-phase mixture. In the case in which the amount of water is very low, it is possible for all of this water to be trapped by the cells and for the reaction medium to be assimilated into a suspension of cells in an organic medium (medium defined as microaqueous). The volumetric oil-to-water ratio can vary greatly. In the case of an emulsion, it can be obtained using surfactants or with mechanical systems. As a general rule, the mixture is brought to ambient temperature and atmospheric pressure.

In fact, any desulfurization process described can be used, since the improvement is caused by the biocatalyst itself which is more stable than the biocatalysts described in the prior art.

The desulfurization process described in this invention can be performed on crude oils or on fractions that are obtained from atmospheric distillation or vacuum distillation or on gasoils that are obtained from desulfurization units (HDS) to which it is desired to apply deep desulfurization, or on any other feedstock whose sulfur content must be reduced.

The desulfurization process in this invention can be carried out in batch mode or in fed-batch mode or continuously and includes the unitary operations described below:
1) Culture of bacteria The biocatalysts are obtained by aerobic culture of the cells in a fermenter. The fermentation can be done in batch mode, in fed-batch mode or continuously. The culture medium contains at least one source of carbon that can be assimilated by the strains described in this document, at least one source of nitrogen and mineral salts. The carbon source can be, for example, glycerol provided in the form of industrial glycerine, ethanol, acetic acid or one of its salts, another organic acid or one of its salts, etc. The nitrogen source consists of ammonium salts or nitrate salts or urea. The culture medium can also contain sources of organic nitrogen, such as yeast extract, corn steep, peptones, etc. as long as their contribution does not cause an excess of sulfate in the culture medium. The mineral salts are present for the purpose of providing the potassium, sodium, magnesium, phosphorus, chlorine, iron, and calcium needed by the strains. The culture medium also contains at least one source of organic or mineral sulfur provided in the most conventional manner to ensure that synthesis of the enzymes responsible for desulfurization is not suppressed, i.e., by ensuring that the sulfate concentration in the culture medium is low, for example less than 50 mg/l. In this case, the organic sulfur source can be DMSO, DBT or any other compound containing organic sulfur molecules that can be assimilated by the strains described in this invention, for example a sulfur-containing gasoil fraction. In the case where culture medium contains too large a concentration of sulfate, for example greater than 50 mg/l, it will be necessary after their culture to incubate the cells in the presence of at least one source of organic sulfur such as dibenzothiophene, for example, before using them to trigger desulfurization activities.

Cells usually grow at temperatures of between 20 and 35° C., preferably around 30° C., while being stirred and aerated, and at a pH around neutral, 5 to 9 for example.

Several fermentation stages are most often necessary before creating the culture in the production fermenter; these stages constitute precultures. They make it possible to gradually progress from low-volume cultures to high-volume cultures. The ratio between the volume of inoculant and the volume of the culture under consideration is the inoculation rate (advantageously between 0.2 and 10%).

For example, the culture of strain CNCM I-2207 can be carried out according to the following protocol:

Precultures are created starting from a pure culture congelate of this strain. When the development of the preculture made it possible to obtain a sufficient biomass, corresponding to, for example, an optical density measured at 600 nm on the order of 5 per culture in batch mode on a medium identical to the one described in Example 1 below, the preculture or a portion of the latter is transferred in a sterile fashion to the biocatalyst production fermenter in such a way as to obtain an inoculation rate of 5%.

The production fermenter initially contains a liquid culture medium containing mineral salts and the usual vitamin supplements, avoiding any presence of sulfates, dimethyl sulfoxide (0.8 g/l) as a source of sulfur, a source of nitrogen (2 g/l of ammonium nitrate) and 5 g/l of sodium acetate as a source of carbon and energy. The concentration of this carbon source could be very low, even zero, if supply of the carbon substrate is begun promptly after inoculation. It should never exceed the inhibiting concentration, for example 15 g/l, in the case of acetate or acetic acid. Then the reactor is fed, preferably continuously, with a sterile aqueous solution containing a 5× concentrated mineral medium (any combined component with the exception of the carbon source) and 6N acetic acid. This solution will be used as a pH regulating agent, whereby the latter is set at 7. Thus, the supply rate is automatically modulated in such a way as not to exceed a residual concentration of organic acid greater than the inhibiting concentration and not to have an acid concentration which remains at zero for long, since the demand for organic acid which is associated with the development of the strain is met by supplying a pH regulating agent. This is the principle of the pH-stat which is then advantageously applied. The fermentation medium is stirred (500 ppm) and aerated, and the temperature of the medium is kept under control in the range of 30° C. Thus, after 90 hours of fermentation, the cell concentration is 18.5 g/l (dry weight) for a consumed carbon substrate of 61.4 g/l of acetic acid.

A carbon source can also be fed independently of the addition of a regulatory agent to ensure that it does not exceed the inhibiting acetic acid concentration, without for all that having a zero residual concentration of acid. It is also possible to continuously draw of f from the culture medium in order to bring about continuous fermentation with organic acid supply.

2) Preparation of the biocatalyst

After culturing in the fermenter, the cells are used as such (culture medium) or are harvested and separated from their culture medium by filtration, centrifuging or decanting, or any other means known to one skilled in the art. They can then optionally be subjected to special preparation treatments such as drying, freeze-drying, permeabilization, or immobilization so that they can be used in the biodesulfurization treatment.

Likewise, the enzymatic desulfurization system could be used instead of entire cells. In this case, an enzymatic extract will be prepared according to the usual methods, such as a simple crushing of cells, followed by centrifuging.

3) Biodesulfurization

The biodesulfurization reaction can be carried out in batch mode or in fed-batch mode or continuously, and in this latter case in a single stage or in a series of reactors. It is possible to use reactors of the air-lift type or stirred reactors that ensure both aeration of the medium (the reaction needs oxygen) and good dispersion of the different contributing phases.

The reaction can be carried out in a two-phase water/oil medium or in an emulsified medium. The volumetric water-to-oil ratio is variable and may fluctuate from 1/99 to 95/5. Water-to-oil ratios between 5/95 and 90/10, and most often between 20/80 and 80/20, are preferable.

The aqueous phase used can consist of at least in part of water that has been recovered after possible removal of sulfates. It can also be obtained from the microorganism culture medium.

The desulfurization reaction is usually carried out at a temperature of between 20 and 40° C., preferably between 25 and 35° C., and at a pH of between 5 and 9, preferably between 6 and 8, and at a pressure of generally between 1 and 3 bar (one bar=0.1 MPa).

The aqueous phase can contain an energy source in order to ensure physiological supply of electrons.

The biocatalyst used consists of any one of the forms described above. It can be obtained from a recycling operation after separation of the contributing phases.

All of these operations can be carried out continuously.

A continuous column reactor can also be used, whereby this reactor is first filled with biocatalyst in solid form, preferably immobilized on a solid support allowing good flow of the feedstock without clogging and ensuring that sufficient humidity is maintained (several %) around the biocatalyst so that it remains active when the feedstock to be treated passes. The feedstock can be passed through in countercurrent.

4) Separation of the phases

The conventional processes allowing separation of an oil phase from an aqueous phase can be applied. The following three phases result:

a) The desulfurized oil phase. The latter can optionally be dehydrated before use.

b) An aqueous phase containing the biocatalyst and optionally sulfates. The latter can optionally be re-used in the first or third stage after optional elimination of sulfates. Since the biocatalysts may be sensitive to sulfate content, the number of times the aqueous phase can be recycled will depend both on this sensitivity and on the concentration of sulfates generated by the biodesulfurization (that is, the sulfur content of the feedstock to be treated). Thus, the acceptable concentration of sulfates in this aqueous phase will depend on the strains used. By way of example, the desulfurization activity of strain I-2204 is not affected by sulfate concentrations equal to 5 g/l.

c) An emulsified phase containing biocatalyst cells in the presence of desulfurized oil and water. This phase, which can be directly recycled, can also be subjected to another separation stage (centrifuging, for example) or to another stage of washing with water, after which the oil and water phases obtained can be assimilated into the corresponding phases described above.

5) Elimination of sulfates

The aqueous phases obtained during the different stages described above are assembled before optional elimination of sulfates. The latter can be precipitated by the addition of elements that generate salts of insoluble sulfates. They can also be subjected to anaerobic biological treatment using sulfate-reducing microorganisms or to aerobic biological treatment.

This invention can be better understood, and its advantages will become more clear by reading the following examples. The latter are given as illustrative and nonlimiting examples of the invention. In particular, in these examples, the sulfur source used to reveal biodesulfurization activities is in all cases dibenzothiophene (DBT). In this case, this compound serves as a model molecule, but the strains described or cited in this invention can obviously be used in any process for biodesulfrization of petroleum feedstocks containing organic sulfur in the form of thiophene, benzothiophene, dibenzothiophene, naphthobenzothiophene, etc., and their derivatives.

EXAMPLE I

Stability of the desulfurization activity of the strain Rhodococcus sp. ATCC No. 53968 (IGTS8) in an aqueous medium (prior art).

The strain Rhodococcus sp. ATTC No. 53968 was cultivated on a liquid medium initially containing 5 g/l of glycerol, 5 g/l of sodium hexahydrate succinate, 2 g/l of $NH_4NO_3$, 0.5 g/l of $KH_2PO_4$, 4 g/l of $K_2HPO_4$, 0.2 g/l of $MgCl_2.6H_2O$, 1 mg/l of $CaCl_2.2H_2O$, 10 mg/l of NaCl, 0.8 g/l of dimethylsulfoxide (DMSO), 10 ml/l of a solution of oligoelements and 1 ml/l of a vitamin solution. The solution of oligoelements contains 0.5 g/l of $MnCl_2$, 0.5 g/l of $FeSO_4.4H_2O$, 0.5 g/l of $ZnCl_2$, 0.5 g/l of $Na_2moO_{44}$, 0.25 g/l of $CuCl_2$, 0.25 g/l of $Na_2WO_4.4H_2O$ and 120 ml/l of 1N HCl. The vitamin solution contains 5 mg/l of biotin, 5 mg/l of thiamin, 2.5 mg/l of calcium pantothenate, 2.5 mg/l of inositol, 2.5 mg/l of niacin, 2.5 mg/l of pyridoxine-HCl and 2.5 mg/l of para-aminobenzoic acid. After sterilization and inoculation, the flasks are incubated at 30° C. while being stirred for about 48 hours. The final optical density (measured at 600 nm) of the cellular suspension is 7, which equals a cellular dry weight concentration on the order of 3 g/l. The cells produced are then recovered by centrifuging at 4° C. at 12000 rpm for 15 minutes. They are then washed with 0.1 M phosphate buffer pH 7, then the residue is kept at 4° C. until it is used (within no later than 20 hours). Bioconversions are performed in test tubes initially containing 50 mg/l of DBT suspended in phosphate buffer with a pH of 7, 0.1 M, containing 2 g/l (dry weight) of cells. DBT is selected as a model sulfur-containing organic molecule. It is added to an ethanol solution at 5 mg/ml, 10 µl of which are added into the bioconversion medium. The reaction volume is 1 ml, and the initial DBT concentration is therefore 50 mg/l. The reaction takes place at 30° C. while being stirred in the presence of air. The concentrations of DBT and of the final product, 2-hydroxybiphenyl (HBP), are determined by high pressure liquid chromatography (HPLC) after the addition of 2 ml of acetonitrile to the entire reaction medium (1 ml). The samples are analyzed after filtration on filters with 0.45 µm pores. The HPLC analysis system consists of an injection loop of 20 µl, a pump for HPLC Spectra-Physics P4000 operating at a flow rate of 1.5 ml/minute, an HPLC C18-Hypersyl ODS 5µ 120 A separation column (150×4.6 d.i.) and a UV Milton Roy Spectro Monitor 2100 detector. The eluant is a mixture of acetonitrile/phosphate buffer of 0.01 M, pH 6 in a ratio of 75/25. DBT and 2-hydroxybiphenyl are detected at two different wavelengths: 232 nm for the DBT and 207 nm for the HBP. The retention times for DBT and HBP are 3.4 minutes and 1.6 minutes respectively. The detector is first calibrated with standard solutions of these two products. To determine the activity of the cells, the disappearance of DBT and the appearance of HBP are followed over time, between 0 and 24 hours. The same number of tubes as determinations of substrate and product concentrations should be prepared, in general after 0 hour, 1 hour, 2 hours, 4 hours, 6 hours and 24 hours of reaction. The reaction is halted by the addition of acetonitrile to the bioconversion tube. Since there is a difference between the rate of disappearance of DBT and the rate of appearance of HBP, the two rates are calculated for each sampling. The rates of disappearance of DBT and of appearance of HBP are linear as a function of reaction time between 1 and 6 hours. The concentrations of each of the two products after two hours of reaction are taken into account in calculating the activities. The activities are calculated in mg of DBT (or HBP) which has disappeared (or appeared) per g of cell (dry weight) and per hour. Control tests are conducted at the same time. The first consists in incubating DBT under the same conditions and in the absence of cells. The second consists in incubating cells under the conditions described, but in the absence of DBT. In both cases, the results show that there is no disappearance of DBT in the absence of biocatalyst and that the biocatalyst cells do not drop back into the DBT or hydroxybiphenyl in the absence of substrate.

Cell stability over time was estimated as follows. After harvesting and washing the cells cultivated on the culture medium described above, the latter are used as promptly as possible. They are then incubated in flasks containing 0.1 M phosphate buffer, pH 7, at 30° C. while being stirred. The reaction volume is 10 ml and the cellular concentration is 2 g/l. For each incubation time for which activity is to be determined (0, 24, 48, 72, and 96 hours), one flask is used. Activity after a certa in incubation time is evaluated by the addition of 50 mg/l of DBT in ethanol solution. To do this, the contents of the flask are distributed in test tubes (1 ml of cellular suspension per tube) in which the desulfurization reaction is initiated by the addition of DBT. The kinetics of DBT disappearance are determined according to the protocol described in the paragraph above.

Table 1 shows the results obtained with strain ATCC No. 53968.

TABLE 1

Effect of incubation in aqueous medium at 30° C. on cells of Rhodococcus sp ATCC No. 53968.

| Incubation time at 30° C. (in hours) | 0 | 24 | 48 | 72 | 96 |
|---|---|---|---|---|---|
| DBT disappearance rate (in mg/g of cells · h) | 5.1 | 3.4 | 0 | 0 | 0 |
| HBP appearance rate (in mg/g of cells · h) | 1.5 | 0.7 | 0 | 0 | 0 |

The activity of the cells can be observed to decrease rapidly over time to be equal to zero at 48 hours of incubation.

EXAMPLE 2

Stability of the desulfurization activity of strain Rhodococcus sp. ATCC No. 53968 (IGTS8) in a two-phase hexadecane/water medium (prior art).

The Rhodococcus sp. ATCC No. 53968 cells used are prepared in a manner identical to the one described in Example 1. Incubation is done under conditions similar to those of Example 1 with the exception of the composition of the medium that contains 50% by volume of hexadecane and 50% aqueous phase (of a composition identical to the one used in Example 1). Incubation is carried out in flasks containing 20 ml of cellular suspension. After 24, 48, 72 and 96 hours, the DBT is added to a flask in such a way as to obtain a concentration of 50 mg/l. The kinetics of DBT disappearance and HBP appearance are determined from the concentrations of these products measured in samples of 3 ml. The latter are centrifuged in such a way as to harvest the organic phase (hexadecane) that is then analyzed by HPLC after filtration (analysis protocol identical to the one in Example 1). These tests in the two-phase medium are carried out in such a way as to determine stability in the presence of an oil phase.

The results obtained are shown in Table 2.

TABLE 2

Effect of incubation in the two-phase medium (50% phosphate buffer/hexadecane) at 30° C. on cells of Rhodococcus sp. ATCC No. 53968.

| Incubation time at 30° C. (in hours) | 0 | 24 | 48 | 72 | 96 |
|---|---|---|---|---|---|
| DBT disappearance rate (in mg/g of cells · h) | 4.1 | 2.3 | 1.6 | 0 | 0 |
| HBP appearance rate (in mg/g of cells · h) | 1.1 | 0.7 | 0.6 | 0 | 0 |

The activity of the cells can be observed to decrease rapidly over time to be equal to zero at 72 hours of incubation.

EXAMPLE 3

Stability of the desulfurization activity of strains I-2204, I-2205, I-2206, I-2207 and I-2208, selected and isolated according to this invention, in an aqueous medium.

The strains described in the text were cultivated using the protocol described in Example 1. In the same way, they were harvested after 48 to 72 hours of culture, then incubated at 30° C. under conditions rigorously identical to those described in Example 1. The analysis methods are themselves also described in Example 1.

It was possible to evaluate the stability of the strains described in this invention, and the results obtained are shown in Tables 3 to 7. Due to the better stability of these strains, the incubation times were extended to 120 hours.

TABLE 3

Effect of incubation in an aqueous medium at 30° C. on I-2204 cells

| | | | | | | |
|---|---|---|---|---|---|---|
| Incubation time at 30° C. (in hours) | 0 | 24 | 48 | 72 | 96 | 120 |
| DBT disappearance rate (in mg/g of cells · h) | 4.2 | 3.4 | 4.0 | 3.9 | 3.2 | 2.7 |
| HBP appearance rate (in mg/g of cells · h) | 2.5 | 0.8 | 0.7 | 0.4 | 0.3 | 0.4 |

TABLE 4

Effect of incubation in an aqueous medium at 30° C. on I-2205 cells

| | | | | | | |
|---|---|---|---|---|---|---|
| Incubation time at 30° C. (in hours) | 0 | 24 | 48 | 72 | 96 | 120 |
| DBT disappearance rate (in mg/g of cells · h) | 4.7 | 3.7 | 3.6 | 3.9 | 3.7 | 2.9 |
| HBP appearance rate (in mg/g of cells · h) | 1.0 | 0.6 | 0.5 | 0.4 | 0.4 | 0.3 |

TABLE 5

Effect of incubation in an aqueous medium at 30° C. on I-2206 cells

| | | | | | | |
|---|---|---|---|---|---|---|
| Incubation time at 30° C. (in hours) | 0 | 24 | 48 | 72 | 96 | 120 |
| DBT disappearance rate (in mg/g of cells · h) | 3.8 | 3.5 | 4.0 | 3.8 | 3.6 | 3.0 |
| HBP appearance rate (in mg/g of cells · h) | 0.5 | 0.5 | 0.4 | 0.3 | 0.3 | 0.3 |

TABLE 6

Effect of incubation in an aqueous medium at 30° C. on I-2207 cells

| | | | | | | |
|---|---|---|---|---|---|---|
| Incubation time at 30° C. (in hours) | 0 | 24 | 48 | 72 | 96 | 120 |
| DBT disappearance rate (in mg/g of cells · h) | 4.4 | 4.0 | 3.6 | 3.7 | 3.1 | 2.9 |
| HBP appearance rate (in mg/g of cells · h) | 3.0 | 1.9 | 1.3 | 1.2 | 0.8 | 0.7 |

TABLE 7

Effect of incubation in an aqueous medium at 30° C. on I-2208 cells

| | | | | | | |
|---|---|---|---|---|---|---|
| Incubation time at 30° C. (in hours) | 0 | 24 | 48 | 72 | 96 | 120 |
| DBT disappearance rate (in mg/g of cells · h) | 3.9 | 3.2 | 3.1 | 3.3 | 3.4 | 3.2 |

TABLE 7-continued

Effect of incubation in an aqueous medium at 30° C. on I-2208 cells

| | | | | | | |
|---|---|---|---|---|---|---|
| HBP appearance rate (in mg/g of cells · h) | 1.5 | 0.7 | 0.5 | 0.4 | 0.4 | 0.3 |

Table 8 synthesizes these results by showing the residual activities after 96 hours of incubation. The results obtained may be compared with those of strain ATCC No. 53968 (Example 1), the residual activity of which was zero after 48 hours of incubation under rigorously identical conditions.

TABLE 8

Residual desulfurization activity of strains I-2004, I-2205, I-2206, I-2207, I-2208 after 96 hours of incubation at 30° C.

| Strain | I-2204 | I-2205 | I-2206 | I-2207 | I-2208 |
|---|---|---|---|---|---|
| % of activity (disappearance of DBT) after 96 hrs of incubation | 76 | 79 | 95 | 70 | 87 |
| % of activity (appearance of HBP) after 96 hrs of incubation | 12 | 36 | 60 | 27 | 27 |

Strains *Rhodococcus erythropolis* I-2204, *Rhodococcus erythropolis* I-2205, *Rhodococcus erythropolis* I-2207, *Rhodococcus erythropolis* I-2208 and *Rhodococcus rhodnii* I-2206 turn out to be remarkably stable.

EXAMPLE 4

Stability of the desulfurization activity of strains CNCM I-2204, I-2205, I-2206, I-2207 and I-2208, selected and isolated according to this invention, in a two-phase (hexadecane/water) medium.

The strains described in the text were cultivated according to the protocol described in Example 1. In the same way, they were harvested and then incubated at 30° C. under conditions rigorously identical to those described in Example 2. The analysis methods are themselves also described in Example 2.

The stability of the strains in the two-phase medium was evaluated by measuring the activities of HBP appearance and DBT disappearance after 96 hours of incubation. The residual activities are shown in Tables 9 to 13.

TABLE 9

Effect of incubation in two-phase medium (50% hexadecane/50% phosphate buffer) at 30° C. on I-2204 cells

| | Disappearance of DBT | Appearance of HBP |
|---|---|---|
| Initial activity (in mg/g of cells · h) | 1.9 | 1.0 |
| Activity after 96 hours (in mg/g of cells · h) | 1.4 | 0.8 |
| Residual activity (%/initial activity) | 74 | 82 |

TABLE 10

Effect of incubation in two-phase medium (50% hexadecane/50% phosphate buffer) at 30° C. on I-2205 cells

|  | Disappearance of DBT | Appearance of HBP |
|---|---|---|
| Initial activity (in mg/g of cells · h) | 1.4 | 1.0 |
| Activity after 96 hours (in mg/g of cells · h) | 1.5 | 0.5 |
| Residual activity (%/initial activity) | 100 | 48 |

TABLE 11

Effect of incubation in two-phase medium (50% hexadecane/50% phosphate buffer) at 30° C. on I-2206 cells

|  | Disappearance of DBT | Appearance of HBP |
|---|---|---|
| Initial activity (in mg/g of cells · h) | 1.3 | 0.7 |
| Activity after 96 hours (in mg/g of cells · h) | 1.8 | 1.1 |
| Residual activity (%/initial activity) | 100 | 100 |

TABLE 12

Effect of incubation in two-phase medium (50% hexadecane/50% phosphate buffer) at 30° C. on I-2207 cells

|  | Disappearance of DBT | Appearance of HBP |
|---|---|---|
| Initial activity (in mg/g of cells · h) | 2.7 | 0.6 |
| Activity after 96 hours (in mg/g of cells · h) | 1.0 | 0.6 |
| Residual activity (%/initial activity) | 35 | 98 |

TABLE 13

Effect of incubation in two-phase medium (50% hexadecane/50% phosphate buffer) at 30° C. on I-2208 cells

|  | Disappearance of DBT | Appearance of HBP |
|---|---|---|
| Initial activity (in mg/g of cells · h) | 2.0 | 1.3 |
| Activity after 96 hours (in mg/g of cells · h) | 0.9 | 0.3 |
| Residual activity (%/initial activity) | 46 | 24 |

Relative to the strain used in the prior art, the desulfurization activities of which were zero after 72 hours of incubation in a two-phase medium, it is noted that the strains described in this invention have clearly improved stability.

EXAMPLE 5

Desulfurization activity of strains IGTS8, I-2204, I-2205, I-2206, I-2207 and I-2208 for 4,6 dimethyl dibenzothiophene.

4,6 Dimethyl dibenzothiophene constitutes a sulfur-containing molecule that is present in gasoil fractions and is very resistant to hydrodesulfurization. We therefore studied its susceptibility to desulfurization by the strains at our disposal. The strains were cultivated and harvested under conditions identical to those described in Example 1. The desulfurization activities on 4,6 dimethyl dibenzothiophene were determined in the same way as on DBT (50 mg/l of substrate, 2 g/l of cells, pH 7, 30° C.). The disappearance of 4,6 dimethyl dibenzothiophene was followed similarly to that described in Example 1 for DBT (HPLC with UV detection at 232 nm).

Table 14 summarizes the activities of 4,6 dimethyl dibenzothiophene disappearance in the various strains tested. In the case of IGT and I-2206 strains, the activities are low and the rate of 4,6 dimethyl dibenzothiophene disappearance was calculated from the residual concentration after 96 hours. In other cases, the rate was calculated as usual over 2 hours.

TABLE 14

Activity of strains on 4,6 dimethyl dibenzothiophene

| Strain | IGT | I-2204 | I-2205 | I-2206 | I-2207 | I-2208 |
|---|---|---|---|---|---|---|
| Rate of 4,6 dimethyl DBT disappearance (in mg/g of cells.h) | 0.04* | 1.2 | 3.6 | 0.17* | 6.3 | 1.3 |

*Rate calculated over 96 hours (instead of 2 hours)

Strains *Rhodococcus erythropolis* I-2204, *Rhodococcus erythropolis* I-2205, *Rhodococcus erythropolis* I-2207, and *Rhodococcus erythropolis* I-2208 have strong activities on 4,6 dimethyl dibenzothiophene, and *Rhodococcus rhodnii* I-2206 has clearly weaker activity than do the other strains, but nevertheless four times greater than that of strain Rhodococcus sp. IGT S8. It therefore appears that the strains selected in this invention have a suitable spectrum of activity with regard to hydrodesulfurization-resistant gasoil compounds.

EXAMPLE 6

Desulfurization activity of strains I-2204, I-2205, I-2206, I-2207 and I-2208 for various gasoils.

The activity of the five strains selected was tested relative to different types of gasoil. The first one is a straight-run untreated gasoil which contains roughly 1.5% sulfur (weight/weight). It was diluted roughly 40 times in hexadecane before being used to lower its sulfur concentration. The others are either straight-run gasoils that are hydrotreated with different levels of sulfur, or straight-run mixtures—LCO (Light Cycle Oils obtained from catalytic cracking) that are also hydrotreated. They are referenced as follows, with the sulfur contents expressed in ppm (weight/weight):

| | | |
|---|---|---|
| S3390 | GO SR (diluted) | Total sulfur = 440 ppm |
| 821-103 | GO SR HDT | Total sulfur = 535 ppm |
| 821-104 | GO SR HDT | Total sulfur = 45 ppm |
| 821-101 | GO SR + LCO HDT | Total sulfur = 660 ppm |
| 215-690A | GO SR + LCO HDT | Total sulfur = 25 ppm |

The tests were conducted in Fernbach flasks stoppered with polyurethane foam stoppers, each flask containing 200 ml of 0.1 M phosphate buffer, pH 7 and 40 ml of gasoil. The cellular concentration was 2 g/l–1 (cells previously frozen to –80° C.). The tests were halted after 96 hours of incubation at 30° C. while being stirred. A control test (without cells) was conducted under the same conditions for each type of gasoil. The total sulfur content of the different samples was determined by Fluorescence X. The results are indicated in Table 15. Table 16 shows the desulfurization rates obtained with the different strains on the five gasoils.

TABLE 15

Sulfur content (in ppm) of gasoils after the action of five selected strains

| Gasoil | Control | I-2206 | I-2204 | I-2205 | I-2207 | I-2208 |
|---|---|---|---|---|---|---|
| 821-103 (SR) | 535 | 500 | 360 | 445 | 380 | 320 |
| 821-104 (SR) | 48 | 42 | 34 | 37 | 32 | 33 |
| 821-101 (SR + LCO) | 670 | 645 | 560 | 630 | 590 | 550 |
| 215-690A (SR + LCO) | 29 | 25 | 16 | 20 | 14 | 18 |
| S3390(a) (SR) | 440 | 400 | 355 | 350 | 330 | 335 |

(a) Gasoil SR at 1.5% sulfur, diluted 40 times in hexadecane

TABLE 16

Desulfurization rate (in %) of gasoils after the action of five selected strains

| Gasoil | I-2206 | I-2204 | I-2205 | I-2207 | I-2208 |
|---|---|---|---|---|---|
| 821-103 (SR) | 7 | 33 | 17 | 29 | 40 |
| 821-104 (SR) | 13 | 29 | 23 | 33 | 31 |
| 821-101 (SR + LCO) | 4 | 16 | 6 | 12 | 18 |
| 215-690A (SR + LCO) | 14 | 45 | 31 | 52 | 38 |
| S3390(a) (SR) | 9 | 19 | 20 | 25 | 24 |

(a) Gasoil SR at 1.5% sulfur, diluted 40 times in hexadecane.

The results show that strains *Rhodococcus erythropolis* I-2204, *Rhodococcus erythropolis* I-2205, *Rhodococcus erythropolis* I-2207, *Rhodococcus erythropolis* I-2208 are very active on the different gasoils. The *Rhodococcus rhodnii* I-2206 strain has weaker activity than the other strains but does have a desulfurization action on the gasoils tested. Moreover, the susceptibility to desulfurization varies depending on the gasoils tested, the most desulfurized gasoil being the one with the lowest percentage of sulfur that is an already extensively hydrotreated gasoil. It thus appears that the strains selected in this invention are quite suitable for desulfurization of petroleum fractions such as gasoil.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 99/07.807 are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for desulfurization of a hydrocarbon feedstock containing sulfur-containing organic molecules by a bacterial culture in the presence of an aqueous phase and in an oxidizing atmosphere, at a temperature of between 20 and 40° C., and at a pH of between 5 and 9, said process comprising the following stages:
   a) the feedstock and the aqueous phase are brought into contact with a biological culture comprising at least one bacterial strain selected from the group consisting of:
   *Rhodococcus erythropolis* CNCM I-2204,
   *Rhodococcus erythropolis* CNCM I-2205,
   *Rhodococcus erythropolis* CNCM I-2207, and
   *Rhodococcus erythropolis* CNCM I-2208,
   and an enzymatic extract thereof, thereby obtaining a reaction medium;
   b) separating from the reaction medium a desulfurized oily phase that is recovered and an aqueous phase containing the biological culture, and
   c) recycling, at least partially, the resultant aqueous phase from stage (b) into stage (a).

2. A process according to claim 1, wherein the reaction medium comprises an emulsified aqueous phase comprising said biological culture, an aqueous phase and an oily phase, said emulsified phase is separated from the reaction medium, and is recycled at least in part into stage a).

3. A process as claimed in claim 2, having residual desulfurization activity of dibenzothiophene at least equal to 10% of the initial activity after 96 hours of incubation in an aqueous medium at 30° C. and at a pH of 7.

4. A process according to claim 1, wherein the strain comprises *Rhodococcus erythropolis* CNCM I-2207.

5. A process according to claim 1, wherein the aqueous phase contains sulfates and wherein substantially all of said sulfates are eliminated.

6. A process according to claim 1, wherein the hydrocarbon feedstock in the presence of water is an emulsion or a non-emulsified two-phase mixture.

7. A process according to claim 1, wherein the volumetric ratio of the aqueous phase to the feedstock is 1/99 to 99/5.

8. A process according to claim 7, wherein the ratio of the aqueous phase to the feedstock is 20/80 to 80/20.

9. A process according to claim 2, wherein the emulsified phase is subjected to a stage of separation or washing, in order to obtain the oily phase, from the aqueous phase and the culture, the culture and the aqueous phase are recycled to stage a), and the oily phase is recovered.

10. A process according to claim 1, wherein at least one of the said bacterial strains is cultured in the presence of at least one source of carbon, at least one source of nitrogen, at least one source of sulfur and of mineral salts at a temperature of between 20 and 35° C., while being stirred and aerated and at a pH of between 5 and 9.

11. A process according to claim 1, wherein the feedstock is crude oil, a petroleum fraction, a distillate or residue from a petroleum refinery distillation or a mixture thereof, or a gasoil obtained from at least one of a conversion and a hydrotreatment unit.

12. A process according to claim 1, wherein the residual activity of desulfurization of the dibenzothiophene presented by the culture is at least equal to 70% of the initial activity after 96 hours of incubation in an aqueous medium at 30° C. and at a pH of 7.

13. A process according to claim 4, wherein the feedstock is a gasoil.

14. A process according to claim 2, wherein the strain comprises *Rhodococcus erythropolis CNCM I*-2207.

15. A process according to claim 9, wherein the strain comprises *Rhodococcus erythropolis* CNCM I-2207.

16. A process according to claim 15, wherein the feedstock is a gasoil.

* * * * *